United States Patent [19]

Hinshaw et al.

[11] Patent Number: 5,545,252
[45] Date of Patent: Aug. 13, 1996

[54] FLOW REGULATION IN GAS CHROMATOGRAPH

[75] Inventors: John V. Hinshaw, New Fairfield; Paul E. Schallis, Ridgefield, both of Conn.

[73] Assignee: The Perkin-Elmer Corporation, Norwalk, Conn.

[21] Appl. No.: 397,707

[22] Filed: Mar. 1, 1995

[51] Int. Cl.⁶ ............................................ B01D 15/08
[52] U.S. Cl. .................. 95/15; 95/22; 95/23; 95/82; 96/102; 96/103; 96/105; 73/23.25; 73/23.27; 73/23.36
[58] Field of Search ............................ 73/23.22, 23.24, 73/23.25, 23.27, 23.35, 23.36, 23.41; 95/14, 15, 19, 22, 23, 82, 83, 89; 96/101–105

[56] References Cited

U.S. PATENT DOCUMENTS

| | | | |
|---|---|---|---|
| 3,496,702 | 2/1970 | Carel et al. | 96/101 X |
| 4,096,746 | 6/1978 | Wilson et al. | 73/205 R |
| 4,802,981 | 2/1989 | Kenney et al. | 96/102 X |
| 4,994,096 | 2/1991 | Klein et al. | 55/20 |
| 5,094,741 | 3/1992 | Frank et al. | 96/101 X |
| 5,108,466 | 4/1992 | Klein et al. | 96/102 X |
| 5,163,979 | 11/1992 | Patrick et al. | 95/19 |
| 5,391,221 | 2/1995 | Fukushima et al. | 95/89 X |
| 5,431,712 | 7/1995 | Henderson et al. | 96/102 X |

FOREIGN PATENT DOCUMENTS

| | | | |
|---|---|---|---|
| 63-131059 | 6/1988 | Japan | 96/101 |
| 0546816 | 3/1977 | U.S.S.R. | 96/102 |

OTHER PUBLICATIONS

"The Effects of Inlet Liner Configuration & Septum Purge Flow Rate on Discrimination in Splitless Injection", John Hinshaw, J. of High Resolution Chromatography 16, p. 249 (Apr. 1993).

"Programmed Temperature Gas Chromatography", Walter E. Harris et al, Wiley (NY), CH 2 pp. 23–29 & 46 (1966).

"Automatic Carrier Gas Control With Self Calibrating Capabilities" P. Magni et al in 16th Int. Symp. on Capillary Chromatography 1, p. 158 (Sep. 27, 1994).

"Flow Programming In Capillary Gas Chromatography", F. Poy in Frigerio et al Recent Developments In Chromatography & Electrophresis Elsevier (1979) p. 187.

"HP 6890 Series GC System" Hewlett Packard Co. Jan. 1995.

*Primary Examiner*—Robert Spitzer
*Attorney, Agent, or Firm*—Herbert S. Ingham; Edwin T. Grimes

[57] ABSTRACT

A gas chromatographic system includes a column and an injector for delivering into the column a test portion of flow. The injector has an exit passage for discharging a split portion of carrier flow. A flow controller for regulating the inlet flow rate includes a variable outlet restrictor for the split portion, a flow rate detector disposed to detect inlet flow rate, and a feedback flow controller to regulate the outlet restrictor to maintain the inlet flow rate substantially constant. Pressure at the inlet to the injector is regulated by detecting pressure at an outlet and providing feedback control to an inlet restrictor. An integral module for the gas components is used on each side of the injector. Calibration and correction for gas characteristics are provided in the feedback for a chromatographic system and for other flow controller regulation.

43 Claims, 5 Drawing Sheets

FLOW REGULATION IN GAS CHROMATOGRAPH

This invention relates to gas chromatography and particularly to a gas chromatographic system with regulation of gas flow.

BACKGROUND OF THE INVENTION

Gas chromatography is essentially a physical method of separation in which constituents of a test sample in a carrier gas are adsorbed and desorbed by a stationary phase material in a column. A pulse of the sample is injected into a steady flow of carrier gas. At the end of the column the individual components are more or less separated in time. Detection of the gas provides a time-scaled pattern which, by calibration or comparison with known samples, indicates the constituents of the test sample. The main components of such a system are the column, an injector with a mixing chamber for introducing the sample into the carrier gas, a detector at the outer end of the column, gas controls and a device such as a computer for treating and displaying the output of the detector. An oven may be used to elevate temperature to maintain the sample in a volatile state, and to improve the discrimination of constituents.

In the use of open tube or packed capillary types of columns, only a small flow of carrier gas with the sample is desired, whereas it is more accurate and convenient to inject larger quantities of the sample. Therefore, a small portion of the gas mixture is bled into the column and the major portion is split off and vented. Such a system is known as a "split injection" system. The injector generally contains a septum through which sample is injected. The mixing chamber usually has an outlet for a purge gas that is a portion of the carrier gas passed along the septum. The purge gas removes vapors emitted from the septum during operation at elevated temperature, as the vapors otherwise could contaminate the carrier and its test sample flowing to the column.

An article "The Effects of Inlet Liner Configuration and Septum Purge Flow Rate on Discrimination in Splitless Injection" by J. V. Hinshaw, J. High Resolution Chromatography 16, 247–253 (Apr. 1993) illustrates several techniques for gas regulation. One is a forward-pressure design in which the carrier gas inlet to the injector is regulated at constant pressure, with mass flow being controlled in the outlet line of the split flow. Another is back-pressure regulated from an outlet line, with mass flow being controlled in the inlet line to the injector. The septum purge is effected through a restriction in the outlet line to maintain small purge flow and a selected pressure in the injector. The restriction may be fixed, or may be a needle valve for adjusting flows in other branches.

Pressure regulators used in gas chromatography are generally known, including older style mechanical devices that utilize spring loaded diaphragms. In newer systems electronic pressure sensors control variable restrictors for flow control to regulate pressure. In gas chromatographs, the pressure typically is generally detected in or proximate the injector. The restrictor of the regulator may be downstream in the same line, or in either of the inlet or split vent lines.

For flow rate controllers, U.S. Pat. No. 4,096,746 (Wilson et al), for example, discloses a mechanical flow controller that contains a diaphragm and a restrictor element in which pressure differential across the restrictor regulates the diaphragm for gas flow. In an electronic system, flow rate is detected by sensing pressure differential across a restrictor element, and the sensor controls an electrically variable restrictor. Heretofore, in current systems, the sensor and restrictor have been disposed in the same line.

A particularly desirable configuration for gas chromatography is the forward pressure design in which the carrier gas inlet to the injector is regulated at constant pressure, with the mass flow being controlled in the outlet line of the split flow. Benefits are improved performance and mass flow discrimination as indicated in the aforementioned article by Hinshaw. However, in this type of system, a mass flow controller including its sensor placed in the vent line has not been practical as it does not function properly in this location. One reason is that the mass flow sensor has a restrictor that creates a pressure drop substantially greater than the desired pressure at the outlet location, so that the back pressure at the injector would be too high. Another is that pressure drop across the restrictor (representing flow detection) is nonlinear in the desired low pressure range of the outlet location, whereas it is essentially linear at higher pressures. Therefore, flow rate in a forward pressure regulated system has generally been set manually by use of a needle valve in the split vent line.

SUMMARY

An object of the invention is to provide an improved gas chromatographic system having control of flow rate in the split vent output line of the injector element of the system. Another object is to provide a gas chromatographic system having forward pressure control and a novel arrangement for flow rate control. A further object is to provide a gas chromatographic system having improved accuracy and mass discrimination in testing of samples. Yet another object is to provide a feedback control for a gas flow rate regulator having improved calibration and sensitivity.

The foregoing and other objects are achieved, at least in part, by a gas chromatographic system including a gas chromatographic column and an injector. The injector has an inlet passage receptive of a carrier gas, a sample inlet selectively receptive of a test sample, and a mixing chamber for receiving the sample to form a mixture in a continuing flow of the carrier gas. The injector further has a column passage for delivering into the column a test portion of the continuing flow, and an exit passage for discharging a split portion of the continuing flow from the mixing chamber. A gas inlet line conveys the carrier gas from a source thereof into the inlet passage at a regulated inlet flow rate.

A flow control means for regulating the inlet flow rate comprises a variable outlet restrictor connected between the exit passage and an ambient space, a flow rate detector disposed in the inlet line to detect the inlet flow rate, and a feedback flow controller operatively disposed between the flow detector and the outlet restrictor. The controller regulates the outlet restrictor with respect to inlet flow rate so as to maintain the inlet flow rate substantially constant, preferably as a constant mass flow rate.

The system preferably further includes a pressure control means for regulating carrier gas flow into the inlet passage so as to maintain a substantially constant pressure at inlet point of the column passage. More preferably, the pressure control means comprises a variable inlet restrictor disposed in the inlet line between the flow rate detector and the inlet passage, and a column pressure detector disposed to detect column pressure substantially at the inlet point of the column. A feedback pressure controller is operatively disposed to regulate the variable inlet restrictor with respect to the column pressure so as to maintain the column pressure substantially constant. The system preferably also includes a separate purge line communicating with the mixing chamber for purging gas, for example from across a septum in the injector. It further is advantageous for the system to have an integral inlet gas module and an integral outlet gas module, wherein the inlet module comprises the fixed inlet restrictor, the variable inlet restrictor and the differential pressure detector, and the outlet module comprises the variable outlet restrictor and the column pressure detector.

In further embodiments, method and means are provided for calibrating the differential pressure as a function of mass flow rate of carrier gas through the fixed inlet restrictor. A set differential pressure is calculated with the function from a predetermined set mass flow rate. A difference signal is generated that is representative of the difference between the differential pressure and the set pressure during operation of the system. The difference signal is utilized to regulate the variable outlet restrictor so as to maintain the differential pressure substantially equal to the set pressure during operation of the system, whereby the inlet flow rate is maintained substantially constant at the set mass flow rate. More preferably, a corrected mass flow rate is computed from the set mass flow rate, the correction being changes with respect to characteristics of the carrier gas from that of the carrier gas during the step of calibrating. These embodiments are more generally applicable to flow control systems where the fixed restrictor with differential detector are not necessarily separated from the variable restrictor by an injector or the like.

DETAILED DESCRIPTION

Figure 1:
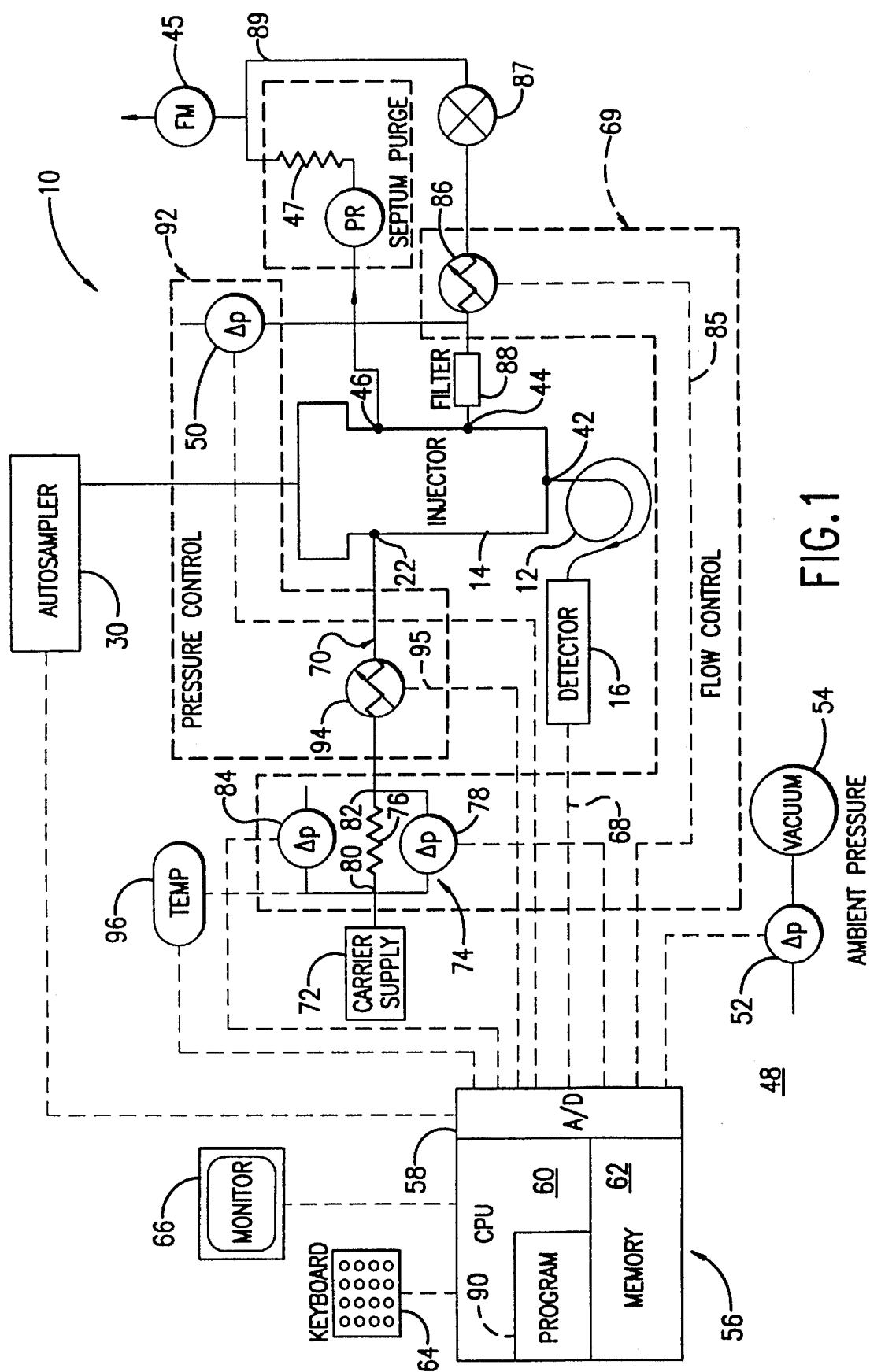
FIG. 1 is a schematic drawing of a gas chromatographic system according to the invention.

In a gas chromatographic system 10 illustrated in FIG. 1, a chromatographic column 12 is connected between an injector 14 and a detector 16. The system is generally a split flow type, as explained below. The column, injector and detector are conventional, such as those associated with a Perkin-Elmer Auto System GC equipped with an autosampler for sampling selected sources of test material. A type of column that particularly utilizes split flow is a capillary column. For example, the column may be formed of a 25 m long fused silica tube 0.32 mm internal diameter with a 5 μm film of polydimethylsiloxane stationary phase. The column alternatively may be a packed open tubular column. The detector may be, for example, a hot wire, a flame ionization or an electron capture type; however, the actual detector is not critical to the present invention.

Figure 2:
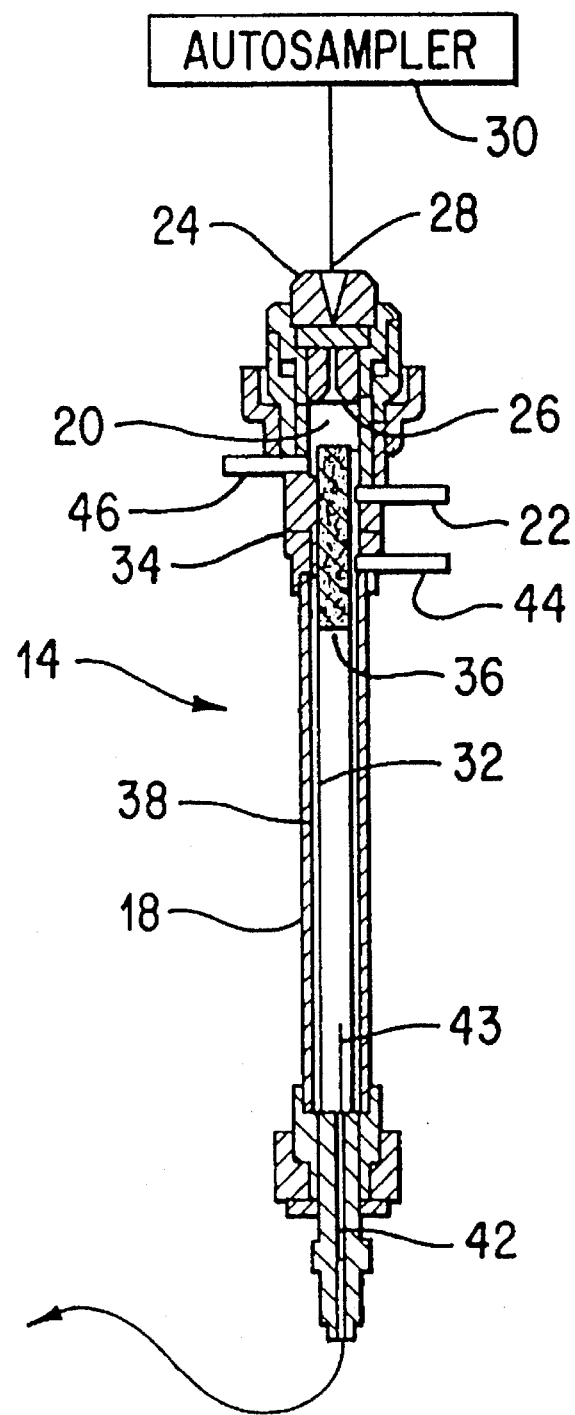
FIG. 2 is a longitudinal section of a conventional injector utilized in the system of FIG. 1.

The injector means 14 (FIG. 2), which is conventional, is constructed typically of a tubular housing 18 with a mixing chamber 20 near the top (as shown, orientation not being important). The mixing chamber is receptive of a carrier gas through an inlet passage 22. At an injection fitting 24 above the chamber is a septum 26 which is a thick (about 0.5 cm) silicone rubber disk. Test sample material, generally a liquid that becomes vaporized or atomized, is selectively injected with a syringe 28 through the septum by hand or from the autosampler 30 into the carrier gas to form a mixture. Sample material generally is injected only momentarily, so that the mixture is a pulse in the continuing flow of the carrier gas.

A glass tube 32 is retained in the housing with an o-ring 34 near the top but below the inlet 22. A short length (e.g. about 1 cm) of glass fiber 36 sits in the top of the tube to enhance mixing. The carrier gas (selectively containing a pulse of sample) flows through the tube down to the bottom of the injector. A fitting 42 holds the column at the bottom. The inlet point 43 for the column taps a small test portion of the continuing flow of carrier gas that contains injected sample to be pass into the column. Most or all of the balance of the carrier gas (with any sample therein) flows up through an annular passage 38 between the housing and the tube, and is passed out of an exit passage 44. It will be appreciated that details of the injector may differ from this example.

Unless turned off externally, a split portion of the carrier gas is discharged through the passage 44. Splitting is done to allow accurate gas regulation and a practical amount of sample to be taken, while reducing the amount of sample that the column may tolerate. The carrier gas, for example, may be helium, nitrogen, hydrogen, air, or mixture such as argon and methane. As the present system provides its own gas controls, the carrier supply pressure into the system 10 need not be accurately maintained. Carrier flow rate, for example, may be 100 ml/min, with 1 ml/min being tapped to the column.

As indicated above, the mixing chamber 20 may be bounded on one side by a septum 26 for the injection. In such a case, the chamber should have an outlet passage 46 for a purge gas taken as a portion of the carrier gas passed along the septum. The purge gas, with a typical flow rate of about 2 ml/min, removes vapors emitted from the septum during operation at elevated temperature, vapors that otherwise could contaminate the carrier and its test sample flowing to the column. The purge gas passes through a fixed restrictor 47, such as a sintered, porous metal element, to an ambient space 48. (As used herein and in the claims, the term "ambient space" designates any region or condition at lower pressure than the system, and usually is the atmosphere, but may be a vacuum chamber, or a plenum to collect and filter the outflow, or any other subsequent arrangement to dispose, use or test the outflow.)

A carrier supply source 72 including an ordinary pressure regulator (either mechanical or electrically controlled, not shown) maintains a constant pressure into the restrictor 47, so as to maintain the purge gas at a constant flow rate. A flowmeter 45 is disposed between the restrictor 47 and the ambient space.

A pressure detector 50 measures the pressure substantially at the inlet point 43 (FIG. 2) of the column passage 42. To achieve this, the pressure detector may be disposed anywhere conveniently in direct communication with the column inlet point 43, for example at the inlet 22, the purge passage 46 or the exit passage 44. The exit passage is preferable because it provides the closest practical pressure location to the inlet point. A similar detector 52 also should be provided to measure actual ambient pressure relative to vacuum 54.

In operation, sample injection to the column are achieved with regulation of both pressure and flow rate. Preferably the operations are effected by a computer 56 including analog/ digital converters 58 as required for input and output (with appropriate amplifier circuits) a processing unit 60 (CPU) memory 62 a keyboard 64 or other means for operator input, and a display by a monitor 66 and/or printer. The computer also processes and displays results from signals on an electrical line 68 from the column detector 16 which shows variations in its output depending on the injection of sample and its selective adsorption and desorption by, or partitioning into and out of, the active element in the column. It further is desirable to display operating pressures, and to compute and display relative flows, particularly mass flow rates and the "split ratio" (portion of split flow to total). Generally an appropriate computer with programming software and/or firmware is provided with a commercial chromatographic system, such as a Perkin-Elmer Model 1022 GC Plus integrator, which uses an Intel™ 80386 processor with "C" programming. For computing capacity in the present application, a second processor may be utilized.

A flow control means 69 includes a flow rate detector, a variable flow rate restrictor and a feedback flow controller there between for closed loop operation. A gas inlet line 70 is disposed for conveying the carrier gas at a selected inlet flow rate from the gas source 72 to the inlet passage 22 into the injector 14. A flow rate detector 74 is located in the inlet line to detect the inlet flow rate. This detector advantageously comprises a fixed gas restrictor element 76 inserted in the inlet line 70, and a differential pressure detector 78 connected across, i.e. in parallel to each end 80, 82 of, the fixed restrictor. Another pressure transducer 84 is used to measure inlet pressure to the flow detector. With the restrictor 76 being calibrated, a proportional signal from the differential detector provides a direct measure of the inlet flow rate. The restrictor may be a capillary tube, but preferably is a laminar flow type advantageously formed of a 0.64 by 0.64 cm plug of sintered porous type 316 stainless steel that provides a flow, for example, of 100 ml/min helium at 6.3 kg/cm$^2$ (90 psi) input with 0.7 kg/cm$^2$ (10 psi) drop across the restrictor. Other useful rates are from 1 to 300 ml/min. Calibration is effected readily by separately connecting the restrictor into a system with a measured flow rate.

A variable flow restrictor 86 is connected in the split flow outlet between the exit passage 44 and the ambient space 48. This restrictor is a conventional or other desired gas valve device, that can be regulated. A suitable type is a variable orifice effected by an electromagnet moving a rod end over a small hole, such as a Porter Instrument Co. model EPC1001. An alternative is a needle valve on a threaded stem controlled by a stepper motor. For "splitless" flow, a separate solenoid shutoff valve 87 is installed in the line 89 between the restrictor and the flowmeter to ambient atmosphere. A carbon filter 88 should be installed in the outlet line before the restrictor to remove components from the sample that would clog the restrictor.

A feedback flow controller is operatively disposed between the flow detector 74 and the outlet restrictor 86 to regulate this restrictor with respect to inlet flow rate so as to maintain the inlet flow rate constant. In one embodiment the controller is an electronic amplifier that modifies an electrical signal from the detector to send a corresponding current to the restrictor control to adjust the restrictor appropriately. In an advantageous embodiment the controller is incorporated into a portion of the computer program 90 that is utilized to operate the chromatographic system 10 and compute and display results.

The pressure signal from the transducer 78 is passed to the computer. This pressure signal is compared to the pressure set point, and the resulting difference is the error signal which is passed through a standard PID (proportional, integral derivative) control algorithm to compute the necessary restriction control signal. This computes the control signal which is directed through a digital/analog converter (or other signal converter as required) and amplifier to the restrictor control. Preferably, the flow rate that is maintained is a mass flow rate. In such case the computer program includes a modification that calculates the feedback signal to the restrictor from stored information on the gas characteristics, particularly viscosity, carrier supply pressure and gas temperature.

In order to maintain a consistent flow rate through the chromatographic column, a substantially constant pressure should be maintained in the mixing chamber 20. To achieve this, the system further preferably has a pressure control means for regulating carrier gas flow through the inlet passage so as to maintain the constant pressure. This effects a forward pressure regulated mode, which is particularly desirable in conjunction with the flow controller in the split flow.

In a preferred embodiment of a pressure control means 92, a variable inlet flow restrictor 94 is disposed in the inlet line 70, between the flow rate detector 74 and the injector inlet 22. This restrictor may be any type as described above for the outlet restrictor, but need not be the same type. As indicated previously, a pressure detector 50 is disposed to detect outlet pressure substantially at the inlet point 43 of the column passage. A pressure feedback controller is operatively disposed to regulate the inlet restrictor with respect to the outlet pressure so as to maintain the outlet pressure substantially constant, for example at 0.7 kg/cm$^2$ (10 psi) This feedback may be similar to that used for the flow controller, and preferably is incorporated into the computer programming 90.

For better accuracy it also is desirable to account for any variations in ambient pressure. Thus the system should include an additional transducer 52 (which may be the same type as the differential transducer) for measuring absolute pressure of the ambient space relative to vacuum. The feedback pressure controller then further comprises means in the computation responsive to the absolute pressure for compensating for variations therein in regulating the outlet restrictor.

The foregoing system provides for forward pressure regulation which is preferred for reasons of performance and mass flow discrimination as illustrated in the aforementioned article by Hinshaw which is incorporated herein by reference. Moreover, by dividing the flow control means 69 by locating the variable restrictor 86 on the outlet line 44, and the flow detector 74 on the inlet line 70, with feedback regulation therebetween, it has become possible to provide regulated flow control for the split flow outlet. (As pointed out in the Background hereinabove, flow regulation with conventional controllers detecting flow rate in the split flow outlet has not been practical.)

Although an electrically regulated flow controller is particularly suited for carrying out the invention, it is possible to use an adaptation of a mechanical flow controller of the type disclosed in the aforementioned U.S. Pat. No. 4,096,746, incorporated herein by reference. The disclosed controller comprises a diaphragm positioned by springs in compression on either side, a one spring having adjustable compression. A pressure drop is effected through a sintered metal restrictor in the gas inlet, and the pressure drop is applied across the diaphragm. The inlet gas pressure on one side urges the diaphragm to open a channel in a control valve assembly, to effect the controlled flow.

An adaptation of a mechanical flow controller is explained briefly herein for illustration of an alternative means for outlet flow control. In the adaptation, the restrictor is removed from the controller (of the referenced patent). Channelling is provided for the inlet flow to the valve assembly without exerting significant pressure on the diaphragm. The restrictor in the inlet line is then utilized. Pressure taps at the inlet and outlet of the restrictor are led respectively to either side of the diaphragm to regulate the flow from the inlet through the control valve assembly. In this way a mechanical controller may be provided having separated flow control, detection and regulation for incorporation into a system of the present invention.

Figure 3:
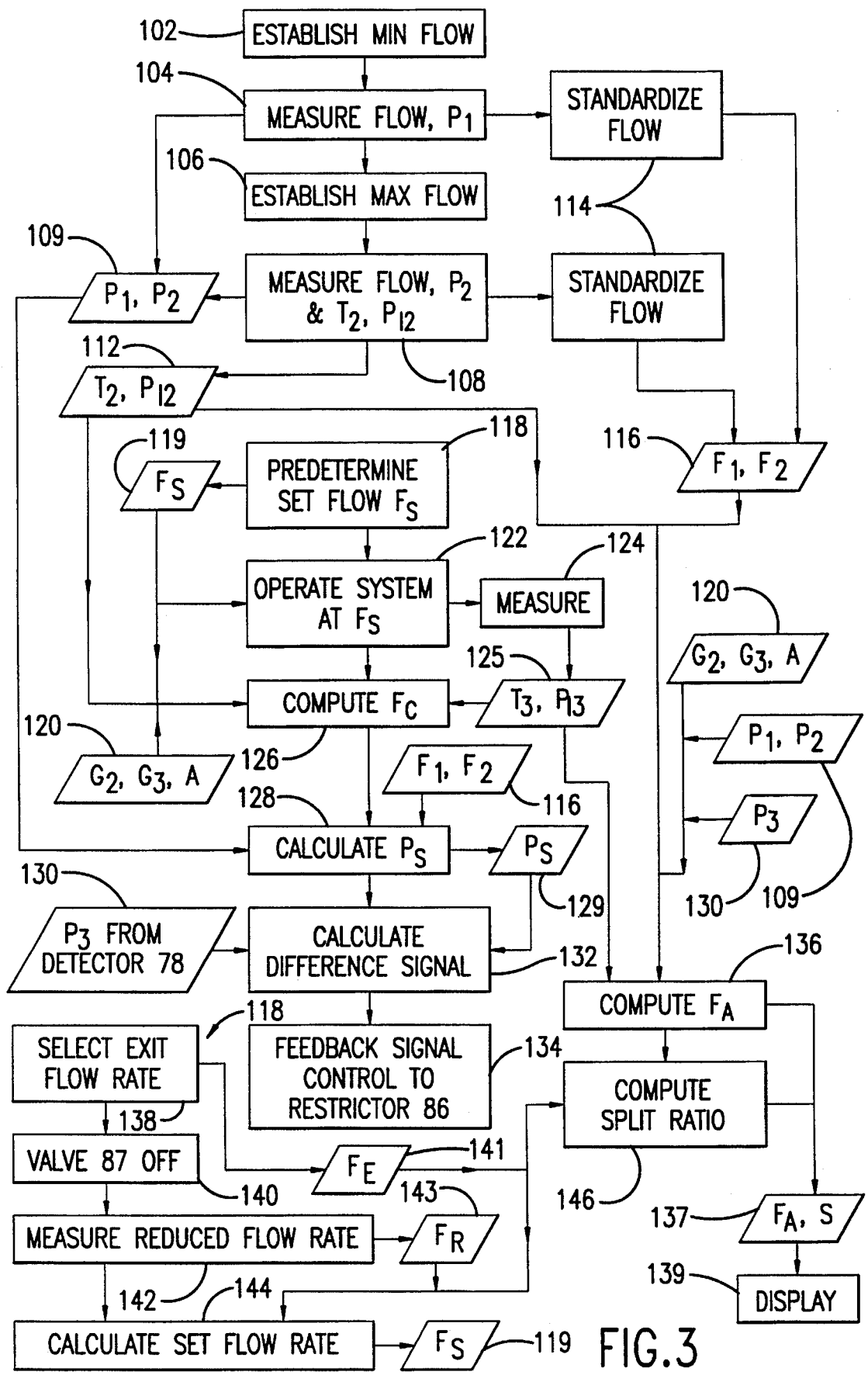
FIG. 3 is a flow diagram for carrying out the invention with the system of FIG. 1.

In further embodiments, means and method steps are provided for effecting feedback control of carrier gas flow. The flow diagram in FIG. 3 illustrates features effected in the computer programming. It will be appreciated that, in the chromatographic system, the programming of the feedback flow controller provides the means and the steps for the feedback and other computations and operations. However, other means such as electronic circuitry may be substituted where practical.

The manufacturer's calibration of the fixed inlet restrictor may be utilized if ordinary accuracy (e.g. about 10%) is sufficient. For accuracy limited only by instruments (e.g. about 1%), further calibration is effected, preferably as described below.

An initial step is calibrating the differential pressure as a function of mass flow rate of carrier gas through the fixed inlet restrictor. First, the column 12 (FIG. 1) is removed from the injector fitting 42 and the hole is plugged. The flowmeter 45, which is previously calibrated, is thereby situated to measure mass flow rate of carrier gas through the fixed inlet restrictor. With the flowmeter, a first calibration flow rate is established 102, and the actual flow rate and a first calibration pressure $P_1$ are measured 104 with the differential detector 78, the calibration pressure being the differential pressure across the fixed inlet restrictor 76. A second calibration flow rate is established 106, and the actual flow rate and a second calibration pressure $P_2$ are measured 108. The differential pressures are stored 109. For reasons indicated below, temperature $T_2$ of the second gas flow from the thermometer 96 (FIG. 1), and inlet pressure $P_{I2}$ from the gage 84, are each measured 108 and stored 112.

The first calibration rate should be a minimum (low) flow rate, generally at or almost zero flow with the variable pressure control restrictor 94 off (small leakage through the turned-off restrictor being possible). The second calibration flow rate is a predetermined maximum flow rate. This is selected to be a fraction, for example 60%, of the manufacturer's recommended maximum for the restrictor 76. The flow rates are either directed from the flowmeter 45 into the computer if such is possible with the flowmeter, or read by an operator and fed into the computer via the keyboard 64.

The flow rates should be standardized 114 to atmospheric pressure and to standard absolute temperature prior to the step of calculating. These are conventionally standardized by multiplying a measured flow rate by a ratio of actual absolute pressure of the atmosphere (or other ambient space) to standard atmospheric pressure (1.03 kg/cm²–14.7 psi), and by a ratio of standard atmospheric temperature (298° K.) to the actual absolute temperature of the atmosphere. The standardized flows $F_1$ and $F_2$ corresponding respectively to pressures $P_1$ and $P_2$, are stored 116.

Each of the calibration flow rates and pressures collectively are parameters defining a function for calculating a differential pressure ($P_S$) from a flow ($F_C$) through the restrictor. For best accuracy the function may have higher order terms. However, a linear function is adequate for the accuracy contempated herein:

$$P_S = (F_C - F_1) * \frac{(P_2 - P_1)}{(F_2 - F_1)} + P_1 \quad \text{(Eq. 1)}$$

In this case the pressure $P_S$ is a set differential pressure, and the flow $F_C$ is a predetermined flow rate, as explained below. This pressure is stored in the memory 62.

The flow rate $F_C$ in Equation 1 should be a corrected mass flow rate computed from a more basic set rate $F_S$ that is predetermined 118 and stored 119. The set rate may be determined from operator input at the time, or previously stored in the memory. The correction made is for any change in characteristics of the carrier gas used during operation from that of the carrier gas during the step of calibrating. Thus the calculation of set pressure $P_S$ is a calculation with the function (Equation 1) from the set flow rate by way of the corrected flow rate $F_C$. Also stored in memory 120 are characteristic information on the carrier gas or gases used during calibration and operation. Standardized viscosity of the calibration gas is ($G_2$), and for the carrier gas used during operation is ($G_3$) (the same as $G_2$ if the gas is the same). (Standardized viscosity means a ratio of viscosity to that of a selected gas such as helium at standard conditions.) A constant A is a temperature coefficient for the fixed restrictor 76 and accounts for both viscosity and expansion effects. The constant A is determined emperically, generally by the manufacturer of the restrictor element; for example, a value of 0.5%/°C. was deemed suitable for the elements disclosed herein.

The system then is operated 122 normally (with the variable restrictor controlling flow, the column 12 reinserted, and sample injected intermittently) at the predetermined carrier gas flow rate $F_S$ entered into the computer. Gas temperature $T_3$ and the absolute inlet pressure $P_{I3}$ are measured 124 and stored 125. The corrected mass flow rate $F_C$ is computed 126 with an equation:

$$F_C = \frac{F_S}{[1 + A(T_3 - T_2)]} * \frac{P_{I2}}{P_{I3}} * \frac{G_2}{G_3} \quad \text{(Eq. 2)}$$

The set pressure $P_S$ is calculated 128 with Equation 1 and stored 129.

During the normal operation 122, a signal representative of the operational differential pressure $P_3$ is directed 130 from the detector 78 to the computer 56. A difference signal is generated 132 that is representative of the difference between the differential pressure $P_3$ and the set pressure $P_S$ during operation of the system. The difference signal is then utilized 134 by feedback to regulate the variable outlet restrictor 86 so as to maintain the differential pressure substantially equal to the set pressure during operation of the system. The inlet flow rate is thereby maintained substantially constant at the set mass flow rate.

The foregoing calibration function and correction for gas characteristics may be combined to calculate 136 the actual mass flow rate ($F_A$) of the carrier gas through the fixed inlet restrictor 76 with further equations:

$$F_A = F_3 * (P_{I3}/P_{I2}) * (G_3/G_2) * [1 + A(T_3 - T_2)] \quad \text{(Eq. 3)}$$

where:

$$F_3 = [(F_2 - F_1)/(P_2 - P_1)] * (P - P_1) + F_1. \quad \text{(Eq. 4)}$$

and where $P_3$ is the actual differential pressure measured. The actual rate $F_A$ may be stored 137 and/or displayed 139 on the monitor 66.

For the determination 118 of the set flow $F_S$, it is desirable to actually preselect 138 and store 141 an exit flow rate $F_E$ in the split vent line 44. An additional correction is made immediately prior to an operation 122 of the system, preferably less than five minutes prior, for example 30 seconds. For this, the valve 87 in the split vent is shut off 140, and a reduced mass flow rate $F_R$ of the carrier gas is determined 142 and stored 143. The set mass flow rate $F_S$ is obtained 144 by adding the reduced mass flow rate $F_R$ to the preselected exit mass flow rate $F_E$, and stored 119. These steps may be effected automatically by the system computer upon startup. Alternatively and more quickly, but less accurately, a reduced mass flow rate may be estimated or otherwise predetermined and stored, and the same value used regularly instead of making the measurements each time.

The reduced flow rate is the sum of the purge and column flows (plus leakage, if any). The correction establishes the actual flow through the fixed inlet restrictor 76 where the control pressure is being detected, so that the exit flow rate in the split vent exit 44 can be preselected and used as the base flow rate. The values can also be used to calculate 146, store 137 and display a split flow ratio S (ratio of split flow plus column flow to column flow) which is a desired operating parameter for a gas chromatographic system. Doing the preliminary flow correction measurement immediately before an actual run reduces effects of potential drift.

The calibration and feedback technique described above is especially advantageous for a split flow system such as described with respect to FIG. 1. However, the technique is also useful where the variable restrictor and the flow detector components are not divided as by the injector. For example, the combination flow controller may be used in the same inlet line for a non-split flow type of chromatographic system, such as driving a packed column inlet. The technique is generally advantageous for driving flow into a variable backpressure of a gas chromatograph.

It is advantageous to combine components of each of the inlet and outlet sides of the injector. Thus, in a further aspect, the system has an integral inlet gas module and an integral outlet gas module. The inlet module contains the fixed inlet restrictor, the variable inlet restrictor, the differential pressure detector, the gas temperature sensor and the carrier supply pressure gage. The outlet module contains the variable outlet restrictor and the column pressure detector.

Figure 4:
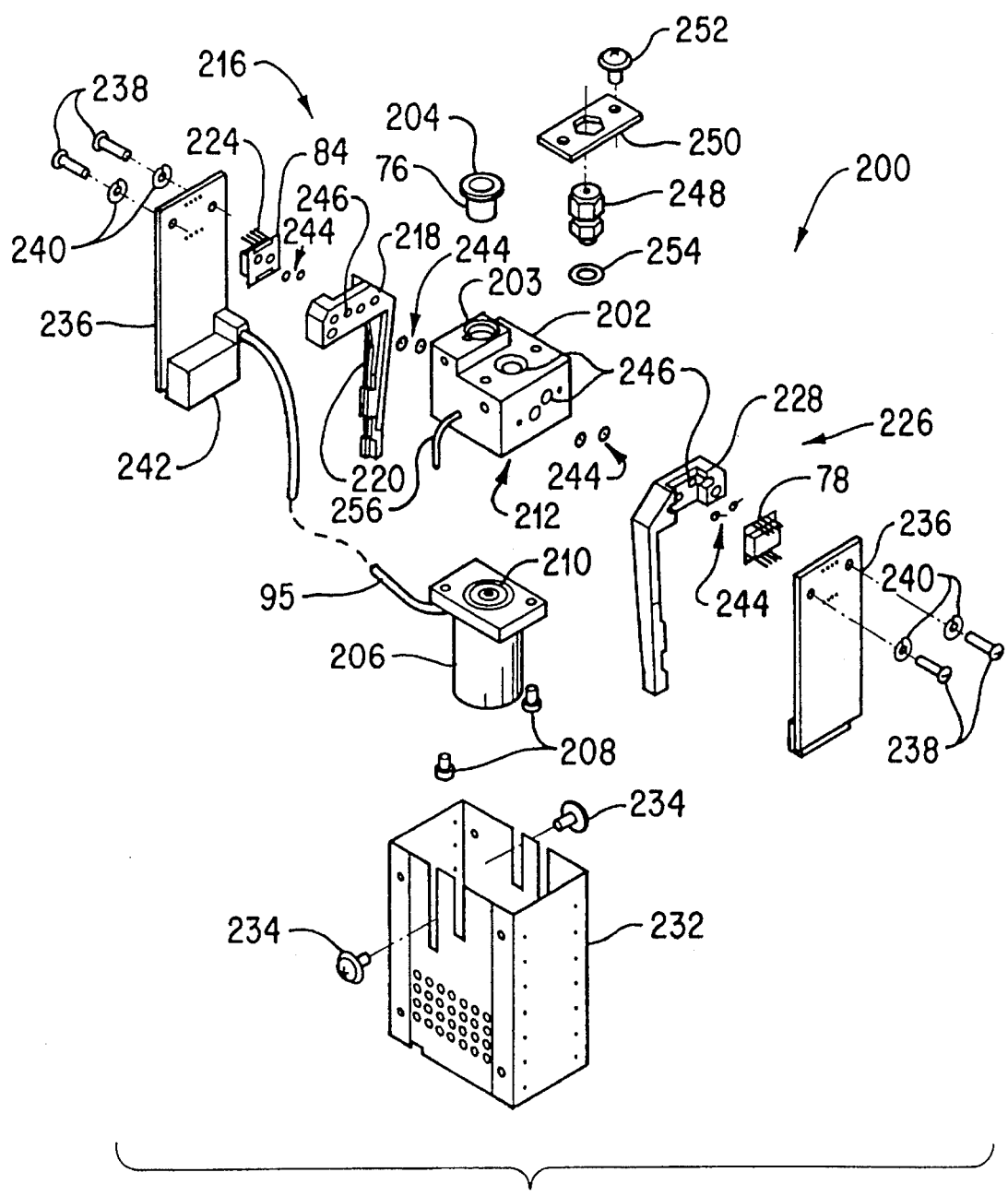
FIG. 4 is an exploded perspective of a first module of components in the system of FIG. 1.
Figure 5:
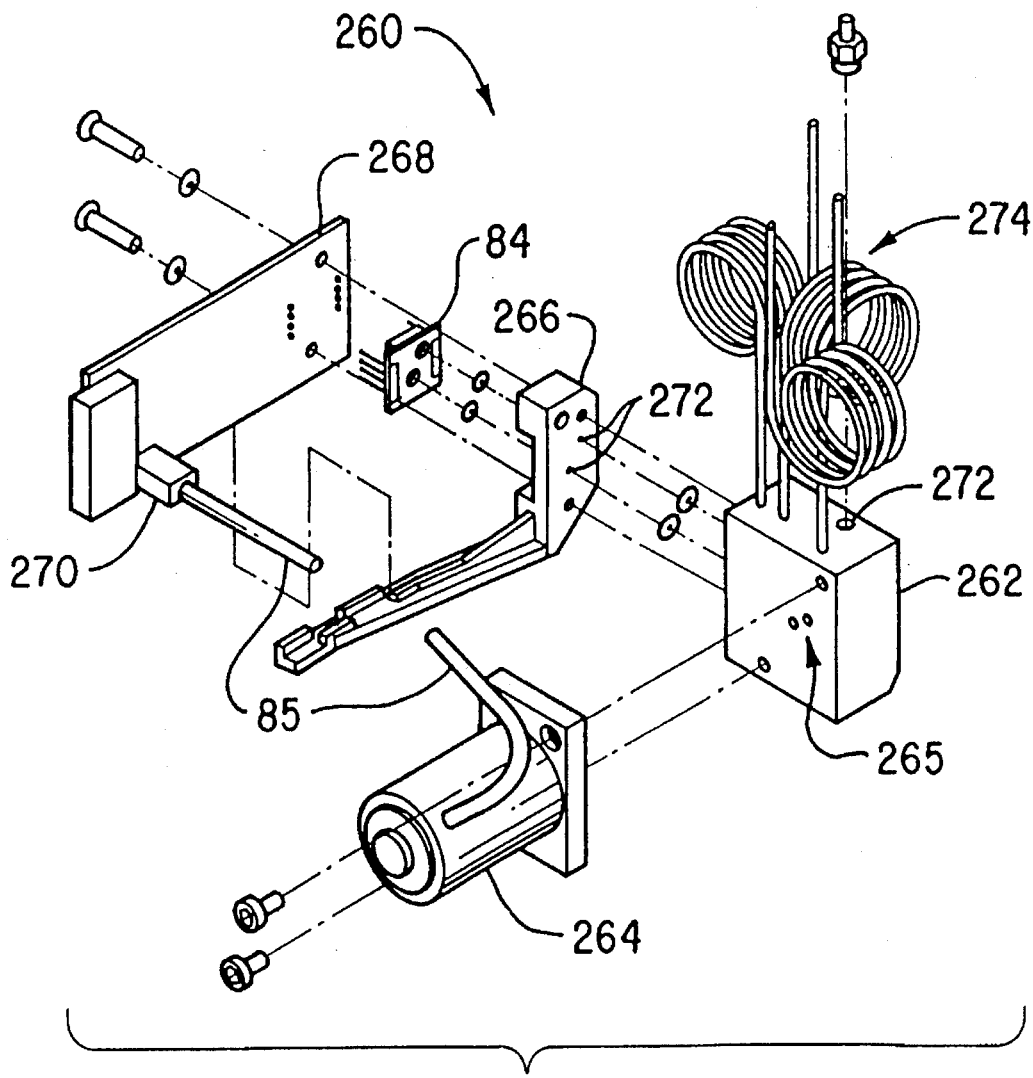
FIG. 5 is an exploded perspective of a second module of components in the system of FIG. 1.

A preferable construction is illustrated for the inlet module 200 (FIG. 4) based on a gas block 202 that has other components mounted thereon. The fixed restrictor 76 is in the form of a porous sintered metal plug sealed into a cylindrical cavity 203 in the block by a threaded disk 204 attached to the plug. A solenoid 206 is fastened under the block by screws 208. A flexible Viton™ diaphragm 210 on the solenoid is held under a pair of orifices 212 in the underside of the block (the orifices not visible in this drawing, but being the same as orifices 265 in FIG. 5). Variable power to the solenoid via a cable 95 varies the flow between the orifices to provide the variable restrictor 94 (FIG. 1).

An end assembly 216 includes an end fitting 218 attached to the block. The fitting includes a mounting bracket 220. The pressure gage 84 (to atmosphere) in the form of a conventional 7.0 kg/cm² (100 psi) silicon transducer e.g. sold by IC Sensors, Milpitas CT, part No. 1210A-100D-3N is mounted on the end fitting so that electrical connectors 224 project accessibly. An opposite end assembly 226 includes a second end fitting 228 with another, similar transducer 78 for measuring differential pressure across the fixed restrictor 76. A housing 232 attached with screws 234 encloses the solenoid and most of the block. End plates 236 are attached with screws 238 and washers 240 over the transducers, and one plate supports an electrical connector 242 for a portion of the cable 95 from the Computer 56 (FIG. 1) to the solenoid. The block and end fittings have appropriate gas passages 246 therein to direct the flows and provide pressure taps in the manner indicated by FIG. 1. O-ring 244 provide further seals where required. A fitting 248 for the carrier gas is held on the block by a plate 250 with a screw 252, sealed by an O-ring 254. An outlet gas tube 256 from the block is similarly provided.

The outlet module 260 (FIG. 5) is similar except that a fixed restrictor and a differential pressure detector are not required and are omitted. A gas block 262 has other components mounted thereon. A solenoid 264, the same type as for inlet module, is fastened to the block (the diaphragm not being visible in FIG. 5). Variable power to the solenoid via cable 85 varies the flow between a pair of orifices 265 to effect the variable restrictor 86 (FIG. 1). An end fitting 266 is attached to the block. The pressure gage 84 (to atmosphere) in the form of a conventional silicon transducer is mounted on the end fitting. An end plate 268 is attached over the transducers and has a connector 270 for the cable 85. The block and end fittings have appropriate other gas passages 272 therein to direct the flows and provide a pressure tap in the manner indicated by FIG. 1. Tubing 274 connected to the block provides for input and output of the split flow and, for convenience, also includes pass-through for the purge.

It will be appreciated that the modules provide a substantial convenience despite the fact that the components in each are not all used together. Thus the differential pressure detector 78 across the fixed restrictor 76 in the inlet module 200 provides signals for feedback control of the variable restrictor 86 in the outlet module 260. Conversely, the pressure gage 50 of the second module 260 provides signals for feedback control of the variable restrictor 94 of the inlet module 200.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method of operating a gas chromatographic system, the system including a gas chromatographic column and an injector, the injector having an inlet passage receptive of a carrier gas, a sample inlet selectively receptive of a test sample, a mixing chamber for receiving the sample to form a mixture in a continuing flow of the carrier gas, a column passage communicating with the column for delivering into the column a test portion of the continuing flow, and an exit passage for discharging a split portion of the continuing flow from the mixing chamber, the system further including a gas inlet line for conveying the carrier gas from a source thereof into the inlet passage at a regulated inlet flow rate, a variable outlet restrictor connected between the exit passage and an ambient space, a fixed inlet restrictor disposed in the inlet line, and a detector of differential pressure (P) connected across the fixed inlet restrictor; wherein the method comprises:

calibrating the differential pressure as a function of mass flow rate of carrier gas through the fixed inlet restrictor, selecting a set mass flow rate ($F_S$) as the inlet flow rate, calculating with the function a set differential pressure ($P_S$) from the set mass flow rate, effecting operation of the system by conveying carrier gas therethrough, generating a difference signal representative of the difference between the differential pressure and the set pressure during operation of the system, and utilizing the difference signal to regulate the variable outlet restrictor so as to maintain the differential pressure substantially equal to the set pressure during operation of the system, whereby the inlet flow rate is maintained substantially constant at the set mass flow rate.

2. The method of claim 1 further comprising computing a corrected mass flow rate ($F_C$) from the set mass flow rate corrected for change in characteristics of the carrier gas from that of the carrier gas during the step of calibrating, wherein the step of calculating comprises calculating with the function the set pressure from the corrected mass flow rate.

3. The method of claim 1 wherein the function is a linear function, and the step of calibrating comprises situating a flowmeter to measure mass flow rate of carrier gas through the fixed inlet restrictor, establishing sequentially with the flowmeter a first calibration flow rate ($F_1$) and a second calibration flow rate ($F_2$), and measuring correspondingly a first calibration pressure ($P_1$) and a second calibration pressure ($P_2$), each calibration pressure being a differential pressure across the fixed inlet restrictor, each said flow rate and said pressure collectively defining the function, the first calibration flow rate being a minimum flow rate associated with utilizing the flowmeter, and the second calibration flow rate being a predetermined maximum flow rate for the fixed inlet restrictor.

4. The method of claim 3 further comprising computing a corrected mass flow rate ($F_C$) from the set mass flow rate corrected for change in characteristics of the carrier gas from that of the carrier gas during the step of calibrating, wherein the step of calculating comprises calculating with the function the set pressure from the corrected mass flow rate.

5. The method of claim 4 further comprising determining temperature ($T_2$) and inlet pressure $P_{I2}$ of the carrier gas into the fixed inlet restrictor during measurement of the second calibration pressure, and determining temperature ($T_3$) and inlet pressure $P_{I3}$ of the carrier gas into the fixed inlet restrictor during operation of the system at the set mass flow rate, wherein the carrier gas used during calibration has a standardized calibration gas viscosity ($G_2$), the carrier gas used during operation of the system has a standardized gas viscosity ($G_3$), and the corrected mass flow rate is computed with an equation:

$$F_C = \frac{F_S}{[1+A(T_3-T_2)]} * \frac{P_{I2}}{P_{I3}} * \frac{G_2}{G_3}$$

and the set pressure is calculated with a second equation:

$$P_S = (F_C - F_1) * \frac{(P_2 - P_1)}{(F_2 - F_1)} + P_1$$

where A is a temperature coefficient for viscosity.

6. The method of claim 5 further comprising standardizing the corrected mass flow rate, the first calibration flow rate and the second calibration flow rate to standard atmospheric pressure and to standard absolute temperature prior to the step of calculating.

7. The method of claim 5 further comprising calculating actual mass flow rate ($F_A$) of the carrier gas through the fixed inlet restrictor with a third equation:

$$F_A = F_3 * (P_{I3}/P_{I2}) * (G_3/G_2) * [1+A*(T_3-T_2)]$$

where:

$$F_3 = [(F_2-F_1)/(P_2-P_1)] * (P-P_1) + F_1.$$

8. The method of claim 1 wherein the system further includes a shutoff valve disposed to shut off flow through the exit passage, and the method further comprises determining a reduced mass flow rate of the carrier gas with the valve shut off, and obtaining the set mass flow rate by adding the reduced mass flow rate to a preselected exit mass flow rate.

9. The method of claim 8 wherein the reduced mass flow rate is determined and the set mass flow rate is obtained immediately prior to operation of the system with injection of a test sample.

10. A method of feedback regulation of gas flow rate through a gas flow controller in a gas line for conveying gas, the controller including a variable restrictor disposed to restrict gas flow in the gas line, a fixed restrictor disposed to restrict gas flow in the gas line, and a detector of differential pressure (P) connected across the fixed restrictor, the method comprising steps of calibrating the differential pressure as a function of mass flow rate of carrier gas through the fixed restrictor, selecting a set mass flow rate ($F_S$) as the inlet flow rate, calculating with the function a set differential pressure ($P_S$) from the set mass flow rate, effecting employment of the regulator by conveying carrier gas therethrough, generating a difference signal representative of the difference between the differential pressure and the set pressure during employment of the regulator, and utilizing the difference signal to regulate the variable restrictor so as to maintain the differential pressure substantially equal to the set pressure during employment of the regulator, whereby the inlet flow rate is maintained substantially constant at the set mass flow rate.

11. The method of claim 10 further comprising computing a corrected mass flow rate ($F_C$) from the set mass flow rate corrected for change in characteristics of the carrier gas from that of the carrier gas during the step of calibrating, wherein the step of calculating comprises calculating with the function the set pressure from the corrected mass flow rate.

12. The method of claim 10 wherein the function is a linear function, and the step of calibrating comprises situating a flowmeter to measure mass flow rate of carrier gas through the fixed restrictor, establishing sequentially with the flowmeter a first calibration flow rate ($F_1$) and a second calibration flow rate ($F_2$), and measuring correspondingly a first calibration pressure ($P_1$) and a second calibration pressure ($P_2$), each calibration pressure being a differential pressure across the fixed restrictor, each said flow rate and said pressure collectively defining the function, the first calibration flow rate being a minimum flow rate associated with utilizing the flowmeter, and the second calibration flow rate being a predetermined maximum flow rate for the fixed inlet restrictor.

13. The method of claim 12 further comprising computing a corrected mass flow rate ($F_C$) from the set mass flow rate corrected for change in characteristics of the carrier gas from that of the carrier gas during the step of calibrating, wherein the step of calculating comprises calculating with the function the set pressure from the corrected mass flow rate.

14. The method of claim 13 further comprising determining temperature ($T_2$) and inlet pressure $P_{I2}$ of the carrier gas into the fixed restrictor during measurement of the second calibration pressure, and determining temperature ($T_3$) and inlet pressure $P_{I3}$ of the carrier gas into the fixed restrictor during employment of the regulator at the set mass flow rate, wherein the carrier gas used during calibration has a standardized calibration gas viscosity ($G_2$), the carrier gas used during employment of the regulator has a standardized gas viscosity ($G_3$), and the corrected mass flow rate is computed with an equation:

$$F_C = \frac{F_S}{[1 + A(T_3 - T_2)]} * \frac{P_{I2}}{P_{I3}} * \frac{G_2}{G_3}$$

and the set pressure is calculated with a second equation:

$$P_S = (F_C - F_1) * \frac{(P_2 - P_1)}{(F_2 - F_1)} + P_1$$

where A is a temperature coefficient for the fixed restrictor.

15. The method of claim 14 further comprising standardizing the corrected mass flow rate, the first calibration flow rate and the second calibration flow rate to standard atmospheric pressure and to standard absolute temperature prior to the step of calculating.

16. The method of claim 14 further comprising calculating actual mass flow rate ($F_A$) of the carrier gas through the fixed restrictor with a third equation:

$$F_A = F_3 * (P_{I3}/P_{I2}) * (G_3/G_2) * [1 + A*(T_3 - T_2)]$$

where:

$$F_3 = [(F_2 - F_1)/(P_2 - P_1)] * (P - P_1) + F_1.$$

17. A gas chromatographic system comprising:

a gas chromatographic column;

injector means having an inlet passage receptive of a carrier gas, a sample inlet selectively receptive of a test sample, a mixing chamber for receiving the sample to form a mixture in a continuing flow of the carrier gas, a column passage communicating with the column for delivering into the column a test portion of the continuing flow, and an exit passage for discharging a split portion of the continuing flow from the mixing chamber;

a gas inlet line for conveying the carrier gas from a source thereof into the inlet passage at a regulated inlet flow rate; and flow control means for regulating the inlet flow rate, comprising a variable outlet restrictor connected between the exit passage and an ambient space, a flow rate detector disposed in the inlet line to detect the inlet flow rate, and a feedback flow controller operatively disposed between the flow detector and the variable outlet restrictor to regulate the variable outlet restrictor with respect to inlet flow rate so as to maintain the inlet flow rate substantially constant.

18. The system of claim 17 wherein the flow rate detector comprises a fixed inlet restrictor disposed in the inlet line, and a differential pressure detector connected to detect differential pressure across the fixed inlet restrictor, the differential pressure being representative of the inlet flow rate.

19. The system of claim 17 wherein the flow feedback controller maintains the inlet flow rate as a constant mass flow rate.

20. The system of claim 17 further comprising a purge line for purging gas from the mixing chamber to the ambient space at a constant flow rate separately from the split portion.

21. The system of claim 17 wherein the column passage has an inlet point, and the system further comprises pressure control means for regulating carrier gas flow into the inlet passage so as to maintain a substantially constant pressure at the inlet point.

22. The system of claim 21 wherein the pressure control means comprises a variable inlet restrictor disposed in the inlet line between the flow rate detector and the inlet passage, a column pressure detector disposed to detect column pressure substantially at the inlet point of the column, and a feedback pressure controller operatively disposed to regulate the variable inlet restrictor with respect to the column pressure so as to maintain the column pressure substantially constant.

23. The system of claim 22 further comprising a purge line for purging gas from the mixing chamber to the ambient space at a constant flow rate separately from the split portion.

24. The system of claims 22 further comprising transducer means for measuring absolute pressure of the ambient space, wherein the feedback pressure controller comprises means responsive to the absolute pressure for compensating for variations therein in regulating the variable inlet restrictor.

25. The system of claim 22 wherein the flow rate detector comprises a fixed inlet restrictor disposed in the inlet line, and a differential pressure detector connected in parallel to the fixed inlet restrictor, whereby the differential pressure is representative of the inlet flow rate, and the feedback flow controller maintains the inlet flow rate as a constant mass flow rate.

26. The system of claim 25 further comprising transducer means for measuring absolute pressure of the ambient space, wherein the feedback pressure controller comprises means responsive to the absolute pressure for compensating for variations therein in regulating the variable outlet restrictor.

27. The system of claim 22 further comprising an integral inlet gas module and an integral outlet gas module, wherein the inlet module comprises the fixed inlet restrictor, the variable inlet restrictor and the differential pressure detector, and the outlet module comprises the variable outlet restrictor and the column pressure detector.

28. The system of claim 17 wherein the feedback flow controller comprises means for calibrating the differential pressure (P) as a function of mass flow rate of carrier gas through the fixed inlet restrictor, means for calculating with the function a set differential pressure ($P_S$) from a predetermined set mass flow rate ($F_S$), means for generating a difference signal representative of the difference between the differential pressure and the set pressure during operation of the system, and means for utilizing the difference signal to regulate the variable outlet restrictor so as to maintain the differential pressure substantially equal to the set pressure during operation of the system, whereby the inlet flow rate is maintained substantially constant at the set mass flow rate.

29. The system of claim 28 wherein the feedback flow controller further comprises means for computing a corrected mass flow rate ($F_C$) from the set mass flow rate corrected for change in characteristics of the carrier gas from that of the carrier gas during the step of calibrating, wherein the means for calculating comprises means for calculating with the function the set pressure from the corrected mass flow rate.

30. The system of claim 28 wherein the function is a linear function, and the means for calibrating comprises a flowmeter situated to measure mass flow rate of carrier gas through the fixed inlet restrictor, means for establishing sequentially with the flowmeter a first calibration flow rate ($F_1$) and a second calibration flow rate ($F_2$), and means for measuring correspondingly a first calibration pressure ($P_1$) and a second calibration pressure ($P_2$), each calibration pressure being a differential pressure across the fixed inlet restrictor, each said flow rate and said pressure collectively defining the function, the first calibration flow rate being a minimum flow rate associated with utilizing the flowmeter, and the second calibration flow rate being a predetermined maximum flow rate for the fixed inlet restrictor.

31. The system of claim 30 wherein the feedback flow controller further comprises means for computing a corrected mass flow rate ($F_C$) from the set mass flow rate corrected for change in characteristics of the carrier gas from that of the carrier gas during the step of calibrating, wherein the means for calculating comprises means for calculating with the function the set pressure from the corrected mass flow rate.

32. The system of claim 31 wherein the feedback flow controller further comprises means for determining temperature ($T_2$) and inlet pressure $P_{I2}$ of the carrier gas into the fixed inlet restrictor during measurement of the second calibration pressure, and means for determining temperature ($T_3$) and inlet pressure $P_{I3}$ of the carrier gas into the fixed inlet restrictor during operation of the system at the set mass flow rate, wherein the carrier gas used during calibration has a standardized calibration gas viscosity ($G_2$), the carrier gas used during operation of the system has a standardized gas viscosity ($G_3$), and the corrected mass flow rate is computed with an equation:

$$F_C = \frac{F_S}{[1+A(T_3-T_2)]} * \frac{P_{I2}}{P_{I3}} * \frac{G_2}{G_3}$$

and the set pressure is calculated with a second equation:

$$P_S = (F_C - F_1) * \frac{(P_2 - P_1)}{(F_2 - F_1)} + P_1$$

where A is a temperature coefficient for the fixed restrictor.

33. The system of claim 32 wherein the feedback flow controller further comprises means for standardizing the corrected mass flow rate, the first calibration flow rate and the second calibration flow rate to standard atmospheric pressure and to standard absolute temperature prior to the step of calculating.

34. The system of claim 32 wherein the feedback flow controller further comprises means for calculating actual mass flow rate ($F_A$) of the carrier gas through the fixed inlet restrictor with a third equation:

$$F_A = F_3 * (P_{I3}/P_{I2}) * (G_3/G_2) * [1+A*(T_3-T_2)]$$

where:

$$F_3 = [(F_2 - F_1)/(P_2 - P_1)] * (P - P_1) + F_1.$$

35. The system of claim 28 further comprising a shutoff valve disposed to shut off flow through the exit passage, means for determining a reduced mass flow rate of the carrier gas with the valve shut off, and means for obtaining the set mass flow rate by adding the reduced mass flow rate to a preselected exit mass flow rate.

36. The system of claim 35 further comprising means for effecting the reduced mass flow rate and obtaining the set mass flow rate immediately prior to operation of the system with injection of a test sample.

37. A gas flow regulator of gas flow rate, comprising a gas line for conveying gas, a variable restrictor disposed to restrict gas flow in the gas line, a fixed restrictor disposed to restrict gas flow in the gas line, a detector of differential pressure (P) connected across the fixed restrictor, and a feedback flow controller operatively disposed between the detector and the variable restrictor to regulate the variable restrictor with respect to inlet flow rate, wherein the feedback flow controller comprises means for calibrating the differential pressure as a function of mass flow rate of carrier gas through the fixed restrictor, means for calculating with the function a set differential pressure ($P_S$) from a preselected set mass flow rate ($F_S$), means for generating a difference signal representative of the difference between the differential pressure and the set pressure during employment of the regulator, and means for utilizing the difference signal to regulate the variable restrictor so as to maintain the differential pressure substantially equal to the set pressure during employment of the regulator, whereby the inlet flow rate is maintained substantially constant at the set mass flow rate.

38. The regulator of claim 37 wherein the feedback flow controller further comprises means for computing a corrected mass flow rate ($F_C$) from the set mass flow rate corrected for change in characteristics of the carrier gas from that of the carrier gas during calibration, wherein the means for calculating comprises means for calculating with the function the set pressure from the corrected mass flow rate.

39. The regulator of claim 37 wherein the function is a linear function, and the means for calibrating comprises a flowmeter situated to measure mass flow rate of carrier gas through the fixed restrictor, means for establishing sequentially with the flowmeter a first calibration flow rate ($F_1$) and a second calibration flow rate ($F_2$), and means for measuring correspondingly a first calibration pressure ($P_1$) and a second calibration pressure ($P_2$), each calibration pressure being a differential pressure across the fixed restrictor, each said flow rate and said pressure collectively defining the function, the first calibration flow rate being a minimum flow rate associated with utilizing the flowmeter, and the second calibration flow rate being a predetermined maximum flow rate for the fixed restrictor.

40. The regulator of claim 39 wherein the feedback flow controller further comprises means for computing a corrected mass flow rate ($F_C$) from the set mass flow rate corrected for change in characteristics of the carrier gas from that of the carrier gas during calibration, wherein the means for computing comprises means for calculating with the function the set pressure from the corrected mass flow rate.

41. The regulator of claim 40 wherein the feedback flow controller further comprises means for determining temperature ($T_2$) and inlet pressure $P_{I2}$ of the carrier gas into the fixed restrictor during measurement of the second calibration pressure, and means for determining temperature ($T_3$) and inlet pressure $P_{I3}$ of the carrier gas into the fixed restrictor during employment of the regulator at the set mass flow rate, wherein the carrier gas used during calibration has a standardized calibration gas viscosity ($G_2$), the carrier gas used during employment of the regulator has a standardized gas viscosity ($G_3$), and the corrected mass flow rate is computed with an equation:

$$F_C = \frac{F_S}{[1+A(T_3-T_2)]} * \frac{P_{I2}}{P_{I3}} * \frac{G_2}{G_3}$$

and the set pressure is calculated with a second equation:

$$P_S = (F_C - F_1) * \frac{(P_2 - P_1)}{(F_2 - F_1)} + P_1$$

where A is a temperature coefficient for the fixed restrictor.

42. The regulator of claim 41 wherein the feedback flow controller further comprises means for standardizing the corrected mass flow rate, the first calibration flow rate and the second calibration flow rate to standard atmospheric pressure and to standard absolute temperature prior to application of the means for calculating.

43. The regulator of claim 41 wherein the feedback flow controller further comprises means for calculating actual mass flow rate ($F_A$) of the carrier gas through the fixed restrictor with a third equation:

$$F_A = F_3 * (P_{F1}/P_{F2}) * (G_3) * [1A * (T_3 - T_2)]$$

where:

$$F_3 = [(F_2 - F_1)/(P - P_1) + F_1.$$

* * * * *